US00PP29374P2

(12) United States Plant Patent
Dekkers

(10) Patent No.: US PP29,374 P2
(45) Date of Patent: Jun. 12, 2018

(54) *EUONYMUS* PLANT NAMED 'EUJACODEK'

(50) Latin Name: *Euonymus japonicus*
Varietal Denomination: EUJACODEK

(71) Applicant: Coen Dekkers, St. Oedenrode (NL)

(72) Inventor: Coen Dekkers, St. Oedenrode (NL)

( * ) Notice: Subject to any disclaimer, the term of this patent is extended or adjusted under 35 U.S.C. 154(b) by 0 days. days.

(21) Appl. No.: 15/530,333

(22) Filed: Dec. 23, 2016

(51) Int. Cl.
*A01H 5/12* (2018.01)

(52) U.S. Cl.
USPC ..... Plt./246

(58) Field of Classification Search
USPC ..... Plt./246
See application file for complete search history.

*Primary Examiner* — Annette H Para
(74) *Attorney, Agent, or Firm* — Samuel R. McCoy, Jr.

(57) ABSTRACT

A new and distinct *Euonymus* cultivar named 'EUJACODEK' which is characterized by the combination of a freely-branching, broad upright growth habit with dense foliage, an abundance of pale yellow juvenile foliage, pale yellow juvenile stems, an abundance of pale yellow intermediate foliage with green venation, intermediate foliage which becomes progressively suffused with green as it matures, dark green and glossy mature foliage, large mature foliage, and the stability of these characteristics from generation to generation.

3 Drawing Sheets

Latin name of the genus and species: The Latin name of the genus and species of the novel variety disclosed herein is *Euonymus japonicus.*

Variety denomination: The inventive cultivar of *Euonymus* disclosed herein has been given the variety denomination 'EUJACODEK'.

BACKGROUND OF THE INVENTION

Parentage: 'EUJACODEK' is a spontaneous whole-plant mutation of *Euonymus japonicus* 'Francien' (not patented) which was discovered in St. Oedenrode, the Netherlands in March of 2014. The mutation was noted for its larger leaves and an abundance of pale yellow juvenile foliage.

Asexual Reproduction: Asexual reproduction of 'EUJACODEK', by way of softwood stem cuttings, was first performed in March of 2014 in St. Oedenrode, the Netherlands. Through two subsequent generations, the unique features of this cultivar have proven to be stable and true to type.

SUMMARY OF THE INVENTION

The cultivar 'EUJACODEK' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'EUJACODEK'. These characteristics in combination distinguish 'EUJACODEK' as a new and distinct *Euonymus japonicus* cultivar:

1. *Euonymus* 'EUJACODEK' exhibits a freely branching, upright growth habit with dense foliage; and
2. *Euonymus* 'EUJACODEK' exhibits an abundance of pale yellow juvenile foliage; and
3. *Euonymus* 'EUJACODEK' exhibits an abundance of pale yellow juvenile foliage; and 4. *Euonymus* 'EUJACODEK' exhibits pale yellow juvenile stems; and
5. *Euonymus* 'EUJACODEK' exhibits an abundance of pale yellow intermediate foliage with green venation, with foliage becoming progressively suffused with green as it matures; and
6. *Euonymus* 'EUJACODEK' exhibits dark green, glossy mature foliage; and
7. *Euonymus* 'EUJACODEK' exhibits mature foliage of a large size.

BOTANICAL DESCRIPTION OF THE PLANT

Figure 1:
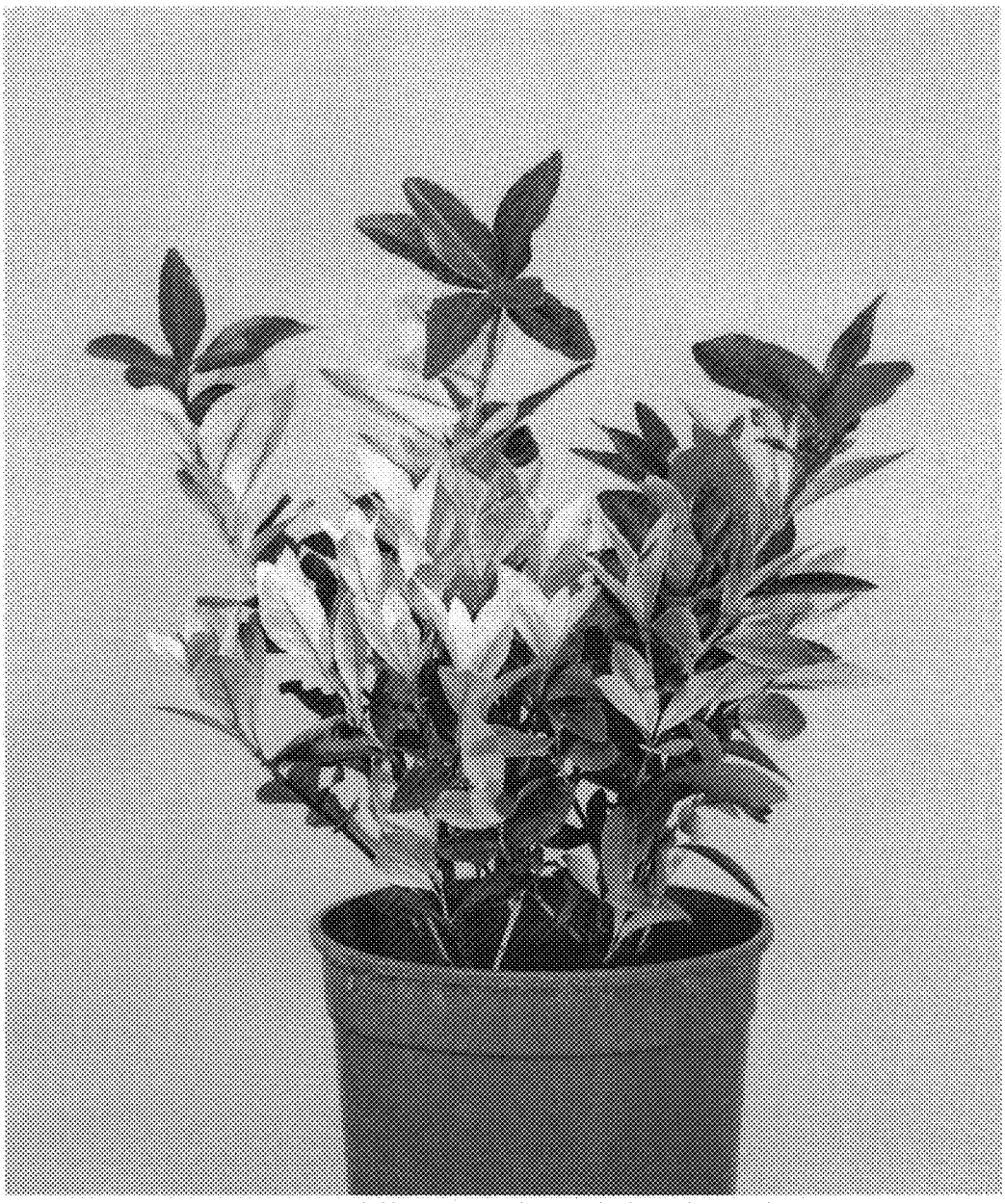
FIG. 1 illustrates, as nearly true as it is reasonably possible to make the same in color photographs of this type, an exemplary plant of 'EUJACODEK' grown in St. Oedenrode, the Netherlands. This plant, grown in a 17 cm nursery container, is approximately one year old from a rooted young plant.
Figure 2:
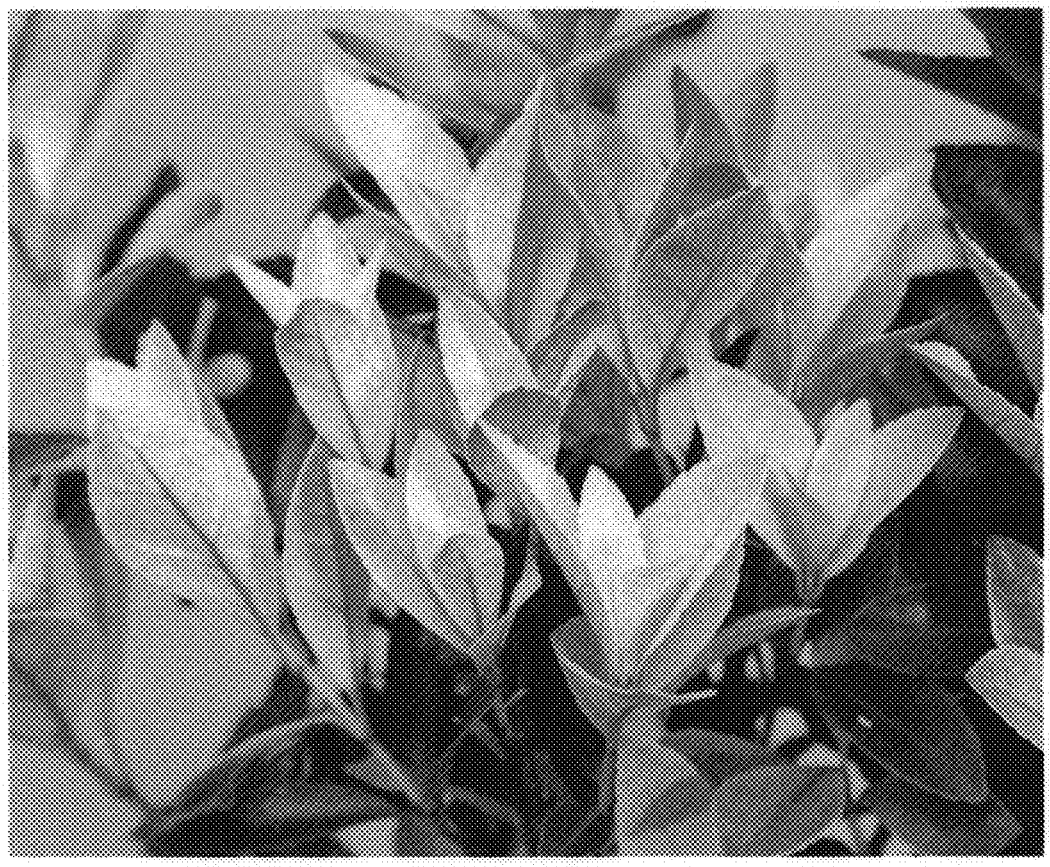
FIG. 2 illustrates, as nearly true as it is reasonably possible to make the same in color photographs of this type, the typical juvenile and intermediate foliage of 'EUJACODEK'.
Figure 3:
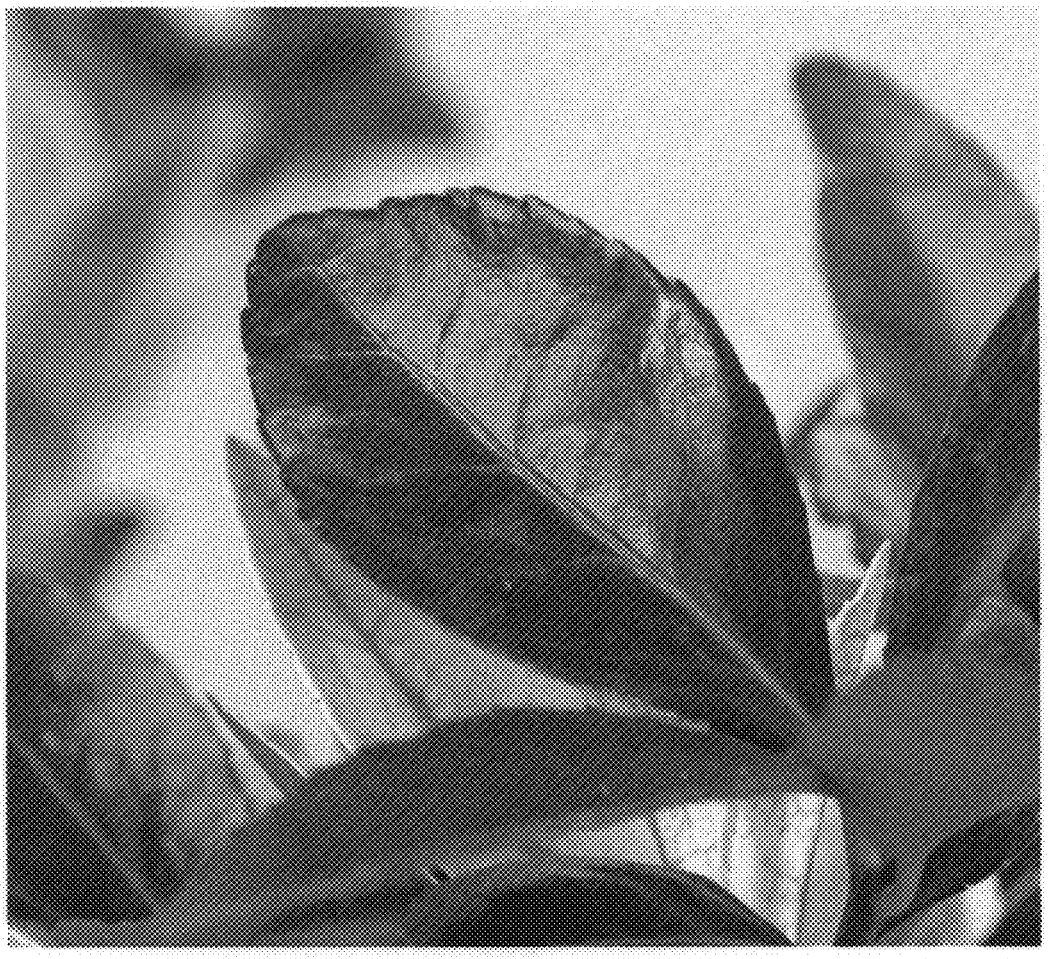
FIG. 3 illustrates, as nearly true as it is reasonably possible to make the same in color photographs of this type, the typical mature foliage of 'EUJACODEK'.

With the exception of the inflorescence and flower descriptions, the following observations and measurements made in June of 2016 describe averages from a sample set of six specimens of one year old 'EUJACODEK' plants grown in 17 cm nursery pots in St. Oedenrode, the Netherlands. Plants were produced under 50 percent shade cloth, using overhead irrigation at regular intervals, and fertilized as required using a slow release fertilizer. No chemical treatments of any kind were utilized.

Those skilled in the art will appreciate that certain characteristics will vary with older or, conversely, with younger plants. 'EUJACODEK' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'EUJACODEK' and comparisons with the parent plants and most similar commercial *Euonymus* cultivar known to the inventor are provided below.

Plant description:

*Growth habit*.—Perennial; broad upright.

*Plant shape*.—Ovate.

*Average height from base to top of foliage*.—31.6 cm.

*Average width*.—Average of 29.6 cm.

*Growth rate*.—Moderate.

*Plant vigor*.—Moderate.

*Propagation details*.—Asexual propagation is accomplished by softwood stem cuttings.

*Time to initiate roots*.—Approximately 21 days are required to initiate roots at 20 degrees Celsius.

*Time to produce a marketable* 17 *cm potted plant*.—Approximately 12 months. Pinching will increase lateral branching.

*Disease and pest resistance or susceptibility*.—Neither tolerance nor resistance to normal diseases and pests of *Euonymus japonicus* have been observed.

*Environmental tolerances*.—Adapt to USDA Zones 8 to 11 and temperatures as high as 40 degrees Celsius; moderate tolerance to rain; moderate to high tolerance to wind.

Root system:

*General*.—Fibrous; freely branched and moderately dense rooting.

*Distribution in the soil profile*.—Shallow to moderately deep.

*Diameter, mature roots*.—0.1 cm, on average.

*Texture*.—Smooth; glabrous.

*Color*.—Greyed-orange, RHS N170A.

Stems:

*Branching habit*.—Main stem grows from the base, freely branching with lateral branches.

*Number of main stems per plant*.—5.

*Number of lateral branches per plant*.—50.

*Appearance and shape*.—Rounded.

*Length of lateral branches*.—10.2 cm.

*Diameter of lateral branches*.—Averaging 0.2 cm at the widest point.

*Internode length on lateral branches*.—1.8 cm.

*Luster*.—Moderately glossy.

*Aspect*.—Average angle is approximately 40 degrees from vertical.

*Strength*.—Strong.

*Color, juvenile*.—Yellow-green, RHS 150D.

*Color, mature*.—Green, slightly darker than RHS 143A.

*Color at internodes*.—Green, slightly darker than RHS 143A.

*Color of oldest wood*.—Greyed-brown, a mixture of RHS N199C and N199A.

*Pubescence*.—Glabrous.

Foliage:

*Arrangement*.—Opposite.

*Division*.—Simple.

*Number of leaves per lateral branch*.—12.

*Lamina*.—Dimensions — 5.3 cm long and 2.7 cm wide, on average. Shape — Elliptical. Aspect — Slightly carinate. Apex — Bluntly acute to narrow obtuse. Base — Short attenuate. Margin — Finely crenate to serrulate. Pubescence, adaxial surface — Glabrous. Texture and luster of adaxial surface — Leathery and moderately glossy to glossy. Pubescence, abaxial surface — Glabrous. Texture and luster of abaxial surface — Leathery and moderately glossy to glossy. Color — Juvenile foliage, adaxial surface — In between yellow-green, RHS 150D, and white, RHS 155A. Juvenile foliage, abaxial surface — In between yellow-green, RHS 150D, and white, RHS 155A. Intermediate foliage, adaxial surface — Yellow-green, RHS 147A, and becoming progressively suffused with green, RHS NN137A, as the foliage matures. Intermediate foliage, abaxial surface — Yellow-green, RHS 146B, and becoming progressively suffused with green, RHS 143A, as the foliage matures. Mature foliage, adaxial surface — Green, RHS NN137A. Mature foliage, abaxial surface — Green, RHS 143A. Venation — Pattern — Pinnate. Color, adaxial surface — Yellow-green, RHS 143C. Color, abaxial surface — Yellow-green, RHS 144A.

*Sheath*.—Not sheathing.

*Petiole*.—Length — 0.7 cm. Width — 0.1 cm. Texture — Glabrous; smooth. Luster — Moderately glossy. Strength — Strong. Color, adaxial surface — Yellow-green, RHS 144C. Color, abaxial surface — Yellow-green, RHS 144B.

Inflorescence: To date, flowering has not been observed.

Flower buds: To date, flowering has not been observed.

Flower: To date, flowering has not been observed.

Reproductive organs: To date, flowering has not been observed.

Seed and fruit: To date, flowering has not been observed.

COMPARISONS WITH THE PARENT PLANT

Plants of the new cultivar 'EUJACODEK' may be distinguished from its parent, *Euonymus* 'Francien' (not patented), which is also the most similar known commercial comparator, by the characteristics described in Table 1.

TABLE 1

| Characteristic | 'EUJACODEK' | 'Francien' |
|---|---|---|
| Growth habit; plant size. | More compact, more freely branched, and spreading; shorter than 'Francien'. | More upright and not as freely branched; taller than 'EUJACODEK'. |
| Stem internode length. | Shorter than 'Francien'. | Longer than 'EUJACODEK'. |
| Leaf size. | Larger than 'Francien'. | Smaller than 'EUJACODEK'. |
| Abundance of foliage. | More abundant. | Less abundant. |
| General coloration of juvenile foliage. | Pale yellow. | Near white. |

That which is claimed is:

1. A new and distinct cultivar of *Euonymus* plant named 'EUJACODEK', substantially as described and illustrated herein.

* * * * *